United States Patent
Cormier et al.

(10) Patent No.: US 6,230,051 B1
(45) Date of Patent: *May 8, 2001

(54) DEVICE FOR ENHANCING TRANSDERMAL AGENT DELIVERY OR SAMPLING

(75) Inventors: Michel J. N. Cormier, Mountain View; Avtar S. Nat, Fremont; Armand P. Neukermans, Palo Alto; Barry Block, Los Altos, all of CA (US)

(73) Assignee: Alza Corporation, Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,153

(22) Filed: Jun. 17, 1997

Related U.S. Application Data

(60) Provisional application No. 60/019,990, filed on Jun. 18, 1996.

(51) Int. Cl.⁷ .......................................................... A61N 1/30

(52) U.S. Cl. ................................ 604/20; 604/46; 600/573

(58) Field of Search ........................... 604/20, 46, 47, 604/239, 264, 272–274; 607/149; 600/573, 575, 576, 345, 309, 347, 365, 373

(56) References Cited

U.S. PATENT DOCUMENTS

| | | | |
|---|---|---|---|
| 3,964,482 | 6/1976 | Gerstel et al. | 128/260 |
| 4,141,359 | 2/1979 | Jacobsen et al. | 128/172.1 |
| 4,250,878 | 2/1981 | Jacobsen et al. | 128/207.21 |
| 4,383,529 | 5/1983 | Webster | 604/20 |
| 4,655,766 | 4/1987 | Theeuwes et al. | 604/896 |
| 4,753,651 | 6/1988 | Eckenhoff | 424/449 |
| 4,756,314 | 7/1988 | Eckenhoff et al. | 128/760 |
| 5,036,861 | 8/1991 | Sembrowich et al. | 128/763 |
| 5,080,646 | 1/1992 | Theeuwes et al. | 604/20 |
| 5,147,296 | 9/1992 | Theeuwes et al. | 604/20 |
| 5,169,382 | 12/1992 | Theeuwes et al. | 604/20 |
| 5,169,383 | 12/1992 | Gyory et al. | 604/20 |
| 5,250,023 | 10/1993 | Lee et al. | 604/20 |
| 5,279,543 | 1/1994 | Glikfeld et al. | 604/20 |
| 5,279,544 | 1/1994 | Gross et al. | 604/20 |
| 5,312,456 | * 5/1994 | Reed et al. | 411/456 |
| 5,362,307 | 11/1994 | Guy et al. | 604/20 |
| 5,438,984 | 8/1995 | Schoendorfer | 128/632 |
| 5,983,136 | * 11/1999 | Kamen | 604/21 |

FOREIGN PATENT DOCUMENTS

| | | | |
|---|---|---|---|
| WO 92/10234 | 6/1992 | (WO) | A61N/1/30 |
| WO 94/05368 | 8/1992 | (WO) | A61N/1/30 |
| WO 96/00110 | 1/1996 | (WO) | A61N/1/30 |
| WO 96/17648 | 6/1996 | (WO) | A61N/1/30 |
| WO 97/07734 | 3/1997 | (WO) | A51B/5/00 |

OTHER PUBLICATIONS

Reiss, Susan M., Biophotonics Internationalm May/Jun. 1997, pp 43–45, "Glucose– and Blood–Monitoring Systems View for Top Spot."

Eppstein, Jonathan, et al., "Rapid Transdermal Drug Delivery with Thermal Micro–Poration," presented at a transdermal delivery conference in San Diego on Dec. 15–18, 1997 and sponsored by IBC.

* cited by examiner

Primary Examiner—Richard K. Seidel
Assistant Examiner—Cris L. Rodriguez
(74) Attorney, Agent, or Firm—Owen J. Bates; D. Byron Miller; Steven F. Stone

(57) ABSTRACT

A percutaneous agent delivery or sampling device comprising a sheet having a plurality of microblades for piercing the skin for increasing transdermal flux of an agent. The microblades having a relatively sharp angled leading edge which transitions to a relatively gradually angled blade edge.

27 Claims, 3 Drawing Sheets

DEVICE FOR ENHANCING TRANSDERMAL AGENT DELIVERY OR SAMPLING

CROSS-REFERENCE TO RELATED APPLICATIONS

A claim is made, under 35 USC §119 (e), to the benefit of the filing of U.S. patent application Ser. No. 60/019,990 filed Jun. 18, 1996.

TECHNICAL FIELD

The present invention relates to transdermal agent delivery and sampling. More particularly, this invention relates to the transdermal delivery of agents, such as peptides and proteins, as well as the transdermal sampling of agents, such as glucose, body electrolytes and substances of abuse, such as but not limited to alcohol and illicit drugs. The present invention uses skin-piercing microblades to enhance the transdermal flux of the agents during transdermal delivery or sampling.

BACKGROUND ART

Interest in the percutaneous or transdermal delivery of peptides and proteins to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to the binding of the polypeptides to the skin. In addition, polypeptides and proteins are easily degraded during and after penetration into the skin, prior to reaching target cells. Likewise, the passive flux of water soluble small molecules such as salts is limited.

One method of increasing the transdermal delivery of agents relies on the application of an electric current across the body surface or on "electrotransport". "Electrotransport" refers generally to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent. The electrotransport of agents through a body surface may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse to a membrane. In many instances, more than one of these processes may be occurring simultaneously to different extents. Electrotransport delivery generally increases agent delivery, particularly large molecular weight species (e.g., polypeptides) delivery rates, relative to passive or non-electrically assisted transdermal delivery. However, further increases in transdermal delivery rates and reductions in polypeptide degradation during transdermal delivery are highly desirable.

One method of increasing the agent transdermal delivery rate involves pre-treating the skin with, or alternatively co-delivering with the beneficial agent, a skin permeation enhancer. The term "permeation enhancer" is broadly used herein to describe a substance which, when applied to a body surface through which the agent is delivered, enhances its transdermal flux. The mechanism may involve an increase in the permeability of the body surface, a reduction in the degradation of the agent (e.g., degradation by skin enzymes) during transport, or in the case of electrotransport delivery/sampling, a reduction of the electrical resistance of the body surface to the passage of the agent therethrough or, the creation of hydrophilic pathways through the body surface.

There have been many attempts to enhance transdermal flux by mechanically puncturing the skin prior to transdermal drug delivery. See for example U.S. Pat. No. 5,279,544 issued to Gross et al., U.S, Pat. No. 5,250,023 issued to Lee et al., and U.S, Pat. No. 3,964,482 issued to Gerstel et al. These devices utilize tubular or cylindrical structures generally, although Gerstel does disclose the use of other shapes, to pierce the outer layer of the skin. Each of these devices provide manufacturing challenges, resistance to easy penetration of the skin, and/or undesirable irritation of the skin.

As has been discussed, a variety of chemicals and mechanical means have been explored to enhance transdermal flux. However, there is still a need to provide a device suitable for increasing transdermal flux which device penetrates the skin with very little insertion force, is low-cost and which can be manufactured reproducibly (i.e., without significant variation from device to device) in high volume production.

DESCRIPTION OF THE INVENTION

The present invention provides a reproducible, high volume production, low-cost device capable of penetrating the skin easily and suitable for increasing transdermal flux. The invention comprises a plurality of microblades for piercing the skin having a leading edge with a relatively sharp angled first segment which transitions to a relatively gradually angled second segment. The particular microblade geometry allows better penetration of the skin with less "push down" (i.e., penetration and insertion) force required of the user. The first segment forms a relatively small angle with respect to an axis extending along the length of the microblade to provide a very pointed section on the blade that pierces the skin readily. The leading edge then transitions to a second segment which forms a larger angle relative to the axis than the first segment. The second segment provides strength to the overall blade to prevent bending due to the wider blade along that portion compared to the portion along the first segment. The second segment, because of its larger width, also forms longer slits in the skin thereby increasing the size of the transdermal pathways through which agents can be delivered or withdrawn. Together, the sharper blade tip and the relatively stronger blade base, improve the overall penetration characteristics of the microblade and thereby reduce the push down force needed to achieve the desired penetration quality.

The blades typically have a length of less than about 0.5 mm and a width and thickness which is even smaller. In spite of their small size, the microblades can be made with an extremely reproducible size and shape so that the microslits formed by the microblades puncturing the skin also have a very reproducible size and depth. Because the microblades have a small thickness (i.e., small relative to the width and length of the blades), the microblades produce less tissue damage for a given cross-section than a skin piercing microneedle having a circular cross-section. The device of the present invention pierces the stratum corneum of a body surface to form pathways through which a substance (e.g., a drug) can be introduced (i.e., delivery) or through which a substance (e.g., a body electrolyte) can be withdrawn (i.e., sampling).

In one aspect of the invention, the device comprises a sheet having a plurality of openings therethrough, a plurality of microblades integral therewith and extending downward therefrom, at least a portion of the microblades having a leading edge with a first angled segment and contiguous with the first angled segment a second angled segment, the first angled segment being located distally on the microblade and having a first angle relative to an axis along the length of the microblade, the second angled segment having an angle greater relative to the axis than the first angle.

The device of the present invention can be used in connection with drug delivery, body analyte or drug sampling, or both. Delivery devices for use with the present invention include, but are not limited to, electrotransport devices, passive devices, osmotic devices and pressure-driven devices. Sampling devices for use with the present invention include, but are not limited to, "reverse" electrotransport devices such as disclosed in Glikfeld et al., U.S. Pat. No. 5,279,543 and Guy et al., U.S. Pat. No. 5,362,307, passive diffusion devices such as disclosed in Schoendorfer, U.S. Pat. No. 5,438,984, osmotic devices such as disclosed in Eckenhoff et al., U.S. Pat. No. 4,756,314, and negative pressure driven devices.

MODES FOR CARRYING OUT THE INVENTION

Figure 1:
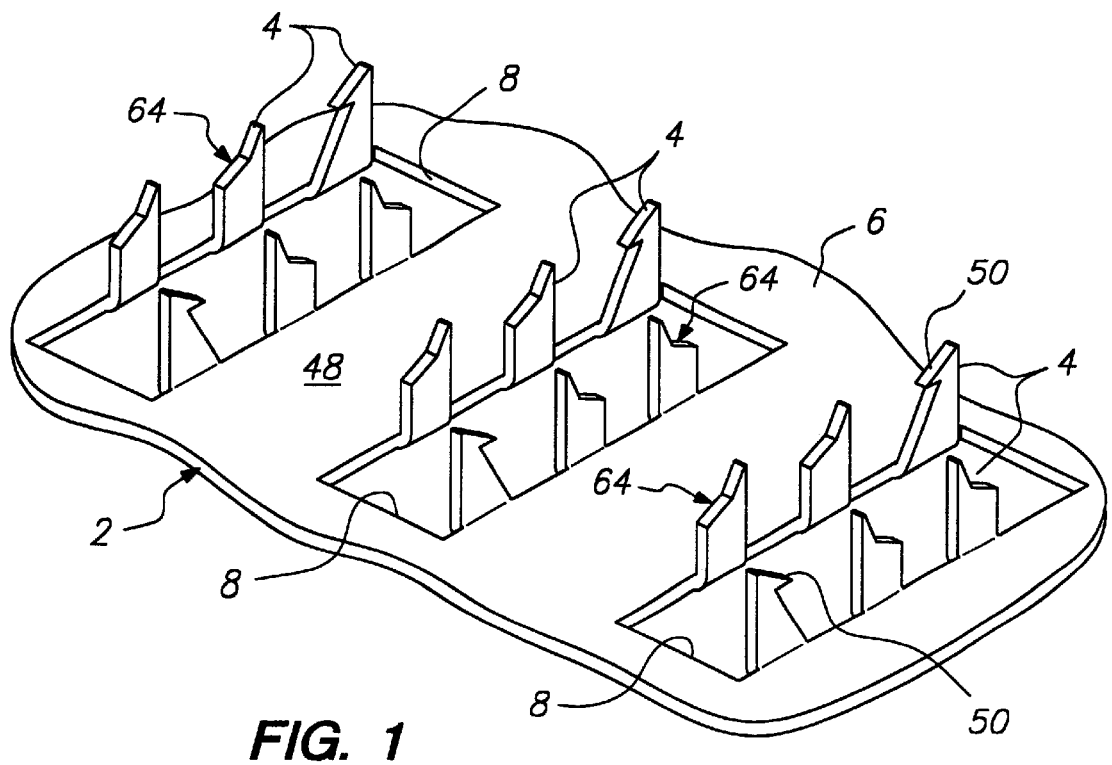
FIG. 1 is an enlarged perspective view of the skin proximal side of the microblade array device in accordance with one embodiment of the present invention.

Turning now to the drawings in detail, one embodiment of the skin-piercing member 2 of the present invention is generally shown in FIG. 1. Member 2 is used in conjunction with percutaneous administration or sampling of an agent. The terms "substance", "agent" and "drug" are used interchangeably herein and broadly include physiologically or pharmacologically active substances for producing a localized or systemic effect or effects in mammals including humans and primates, avians, valuable domestic household, sport or farm animals, or for administering to laboratory animals such as mice, rats, guinea pigs, and the like. These terms also include substances such as glucose, body electrolytes, alcohol, licit substances, pharmaceuticals, illicit drugs, etc. that can be sampled through the skin. The major barrier properties of the skin, such as resistance to drug penetration, reside with the outermost layer (i.e., stratum comeum). The inner division of the epidermis generally comprises three layers commonly identified as stratum granulosum, stratum malpighii, and stratum germinativum.

Once a drug penetrates below the stratum corneum, there is substantially less resistance to permeation through the stratum granulosum, stratum malpighii, and stratum germinativum. The device of the present invention is used to form microslits in the stratum comeum and produce a percolation area in the skin for improved transdermal delivery or sampling of an agent.

Member 2 comprises a plurality of microblades 4 (i.e., a blade array) extending downward from one surface of a sheet or plate 6 (see FIG. 1 in which a portion of member 2 is in an inverted position to show the microblades). The microblades 4 are sized and shaped to penetrate the stratum corneum of the epidermis when pressure is applied to the device. The microblades form microslits in a body surface to increase the administration of or sampling of a substance through the body surface. The term "body surface" as used herein refers generally to the skin of an animal or human.

Figure 2:
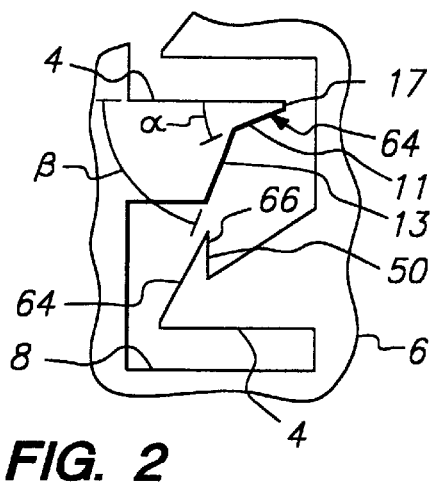
FIG. 2 is an enlarged view of a portion of the microblades of the blade array pattern.

The microblades 4 are generally formed from a single piece of sheet material and are sufficiently sharp and long for puncturing the stratum corneum of the skin. In one embodiment, the microblades 4 and the sheet 6 are essentially impermeable or are impermeable to the passage of an agent. The sheet 6 is formed with an opening 8 between the microblades 4 for enhancing the movement of an agent therethrough. In the case of therapeutic agent (e.g., drug) delivery, the drug is released from a drug-containing reservoir (not shown in FIG. 2) through the opening 8 and passes through microslits formed by the microblades 4 cutting through the stratum comeum, migrates down the outer surfaces of the microblades and through the stratum comeum to achieve local or systemic therapy. In the case of agent (e.g., body analyte) sampling, the analyte migrates from the body through the microslits in the stratum comeum which are cut by the microblades 4.

In one embodiment, the opening 8 corresponds to the portion of the sheet 6 occupied by each of the microblades prior to the blades being transpositioned into the downward depending position. The number of microblades 4 per opening 8 can be any number, preferably however between 1 and about 30 blades per opening. Furthermore, the number of openings per device and the number of blades per device are independent. The device may have only one opening and one microblade. The agent can be administered at a controlled rate of release from the reservoir through an agent release rate controlling material (not shown) covering the openings 8.

As is best shown in FIG. 1, the microblades 4 have a thickness which is much smaller than the width of the blades near their base, i.e., near the point where the blades are attached to the sheet 6. This blade geometry provides maximum drug percolation area with a minimum blade penetration area, and hence less tissue damage. The drug percolation area is the skin area in contact with the blades which provides for drug penetration in the skin. The microblades are shaped with the largest possible surface area with a minimal cross-sectional area so as to give the largest possible percolation area. Thin microblades are better than round protrusions for this purpose because for the same cross-section, a thin blade produces more percolation area and less tissue damage than a protrusion having a circular cross-section (i.e., a cylindrically-shaped protrusion). This is a crucial advantage over the prior art round elements such as needles and tubes. Thin microblades also require less insertion force than round protrusions. The width of each blade can be any of a range of widths. The widths can be different from blade to blade in the array pattern. Likewise, the width can be variable along the length of the blade, as will be described in more detail below. The width of the blade at the intersection of the blade and the body surface after the blade array has been inserted is preferably in the range of about 10 μm to about 500 μm, more preferably about 25 μm to about 400 μm, more preferably 25 μm to about 300 μm.

The microblades 4 are provided with slanted (i.e., angled) leading edges 64 having multiple segments to reduce the insertion force required to press the blades into the skin tissue. Because the blade insertion force is reduced, it is also possible to use a thinner and more flexible sheet 6, which is advantageous in devices adapted to be worn on the skin for extended (e.g., longer than 30 minutes) periods of time. In FIGS. 1–5 and 7, the leading edges 64 have two segments each having a different leading angle. The first segment 11 is the distal most segment. Contiguous with the first segment 11 is second segment 13. The angle of the first segment relative to axis or reference line 15 is designated as $\alpha$. The angle of the second segment is designated $\beta$. The multiple segmented slanted leading edge produces a cut through the skin tissue that is equal to the full width of the blade 4 while reducing the amount of metal that is in the skin tissue. In other words, a flat leading edge (i.e., $\alpha$ is 90°) produces a blade with a larger amount of blade material in the skin tissue than is produced by a blade having a slanted leading edge. The angle a of each segment 11 can be any angle between about 1° to 25°, preferably about 15°. The first segment 11 then transitions to the second segment 13 having an angle $\beta$ between about 26° to 80°, preferably between about 30° to 45°, more preferably 35°.

Figure 3:
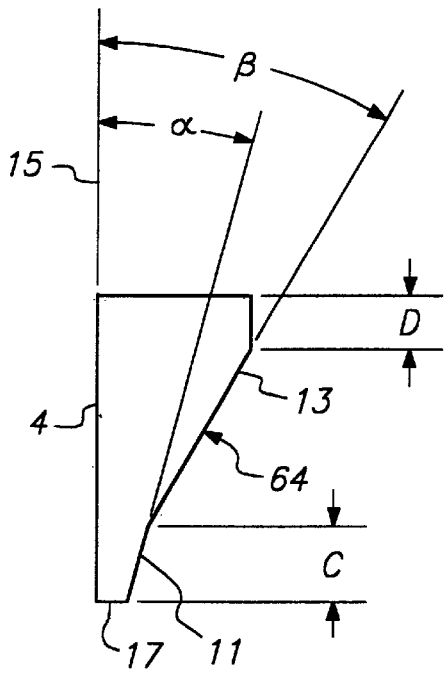
FIG. 3 is an enlarged view of a microblade in accordance with one embodiment of the present invention.
Figure 4:
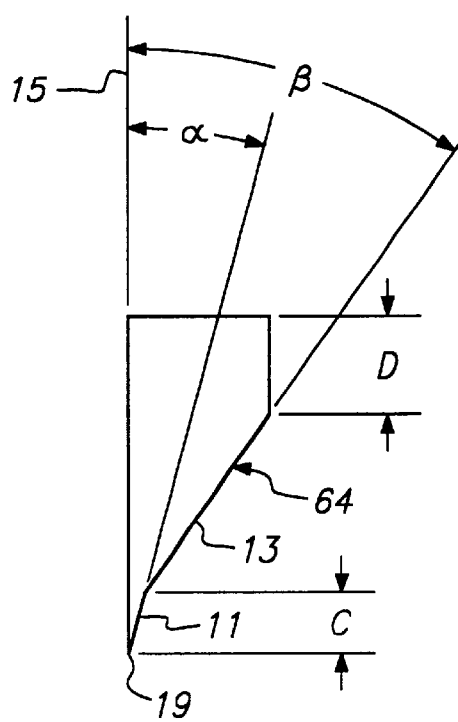
FIGS. 4–7 are enlarged views of other embodiments of the microblade in accordance with the present invention.
Figure 5:
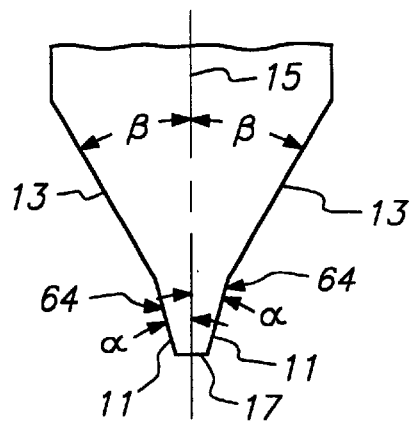
Figure 6:
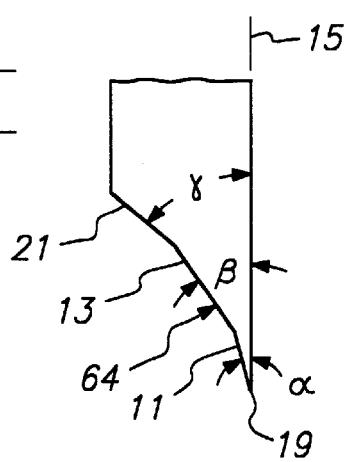
Figure 7:
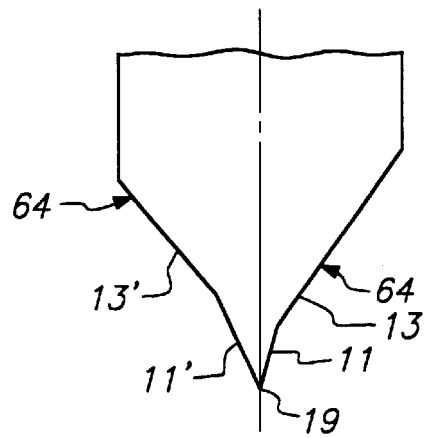

The microblade 4 of the embodiments shown in FIGS. 4, 6 and 7 have sharp distal tips 19 for easy penetration of the skin. The embodiments of microblade 4 shown in FIGS. 1–3 and 5 have a flattened distal most tip 17 which is easier to manufacture and has greater resistance to bending upon insertion in the skin than the more pointed tip 19.

The embodiments of FIGS. 1–4 and 6 have a single slanted leading edge 64 on the microblade 4, whereas the embodiments of FIGS. 5 and 7 have two slanted leading edges 64 beginning approximately on the center line 15 and extending outwardly therefrom on either side of the center line. As shown in FIG. 7, the slanted leading edges need not be symmetrical about the center line. First segment 11' is not equal to segment 11 and second segment 13' is not equal to segment 13.

The multiple segmented leading edge 64 of any of the embodiments previously described can have any number of segments. For example, the embodiment of FIG. 6 has a third segment 21. The angle of the third segment 21 is designated $\gamma$ The second segment 13 transitions to the third segment 21 having an angle $\gamma$ relative to reference line 15 greater than the angle $\beta$. Preferably, angle $\gamma$ is between about 35° to 80°, more preferably about 45°. As can be appreciated from FIG. 6, a plurality of contiguous angled segments wherein each of the subsequent angled segments progressing proximally along the microblade from the first segment has an angle relative to the reference line 15 greater than the angle of the preceding angled segment creates a leading edge which appears arcuate (i.e., curved) in shape. In one embodiment, the leading edge appears curved across the entire width of the blade.

The microblades 4 are formed using a photo-etching process. The photo-etching process allows the microblades 4 to be reproducibly formed on a very small (i.e., tens of microns) scale. This process also allows the microblades 4 to be formed in shapes which require lower force for penetrating the skin. Some of the microblades 4 are provided with barbs 50 (FIGS. 1 and 2) in some fashion so that the member 2 and any corresponding device attached thereto stays attached to the skin after being applied with pressure. The degree of attachment and the number and size of the barbs 50 is such as to retain the delivery or sampling device during the normal activity of the wearer, but not cause pain upon removal. As the microblades are pressed into the skin tissue for use, the leading edge 64 of each microblade 4 cuts through and pushes aside the skin tissue. After the microblades have come to rest in the skin, the skin due to its elastic nature at least partially comes back together around the edges of the microblades 4, in this way the surface 66 on each microblade having a barb 50 engages skin tissue and anchors the device in the skin. If the microblade is left in the skin for an extended period of time (e.g., 24 hours), the skin tissue begins to heal together in the area behind the surface 66 of the barb 50 thus improving the anchoring of the device. Only one barb per blade is shown in the figures but it is within the scope of the present invention that each blade can have a plurality of barbs extending therefrom. The plurality of microblades 4 for puncturing the stratum corneum are present on one face surface 48 of the member 2 in any predetermined arrangement, for example, as a cluster of blades spaced in rows having any desired number, or in any spaced apart relation of one blade to each other. Each blade has a width and thickness that facilitates penetration of the stratum corneum without bending. In the embodiment of FIG. 1, there are six blades 4 along the perimeter of each opening 8 in sheet 6. Preferably, the width of each blade is between about 135 μm to about 300 μm and the length is about 600 μm. The required length of the blades is subject to variation of the body surface being penetrated and corresponds to the natural thickness of the stratum corneum, for one of the principle features of the invention is that the blades are to penetrate the stratum corneum into the epidermis. Usually, the blades will be about 25 μm to about 700 μm in length, with the length for most applications being between about 50 μm to about 600 μm. By way of example, the microblade 4 of FIG. 3 is 254 μm wide and 508 μm in length wherein dimension C is 127 μm and dimension D is 89 μm. The microblade 4 of FIG. 4 is 254 μm wide and 610 μm in length wherein dimension C is 127 μm and dimension D is 178 μm. The sharp distal segment of the microblade is supported by the remainder of the blade as it widens at an angle $\beta$ and provides a relatively large base width which provides the required structural integrity to prevent blade deflection upon insertion and penetration in the skin.

The pattern for any of the blade array devices of the present invention is produced with a photo-etching process. For example, reference may be had to U.S. Provisional Application No. 60/019,990 filed Jun. 18, 1996 of which any of the disclosed methods can be used to produce the member 2 of the present invention. A thin sheet or plate 6 of metal such as stainless steel or titanium is etched photo-lithographically with patterns containing blade-like structures. In general, a thin laminate dry resist or wet resist is applied on a sheet about 7 μm to about 100 μm thick, preferably about 25 μm to about 50 μm thick. The resist is contact exposed using a mask having the desired pattern and is subsequently developed. These operations are conducted in much the same way that they are for the manufacture of a printed circuit board. The sheet is then etched using acidic solutions. After the pattern has been etched through the sheet, the sheet is placed on a die having a plurality of openings corresponding to the openings 8 in the sheet. A punch having a plurality of protrusions corresponding to the openings in the sheet and die is initially located above the sheet and die. At the initial stage, the blades 4 are in the same plane as the rest of the sheet 6. The protrusions on the punch are then pressed into the openings, thus bending the blades 4 downward to be at an angle (e.g., substantially perpendicular) to the plane of the sheet. The finished structure provides blades 4 with an adjacent opening 8 for the passage of a substance therethrough when the member 2 is applied to the skin. Rectangular openings 8 are shown in the figures but the invention encompasses the use of any shape openings including, but not limited to, square, triangular, circular and elliptical. The blades 4 can be patterned with resist on both sides of the sheet 6 and subsequently etched simultaneously from both sides to achieve maximum pattern resolution for a given sheet thickness and to produce a knife-like edge that can not be achieved with conventional stamping and punching processes. Alternatively, the blades 4 can be patterned and etched from one side only.

In another embodiment of the two-sided etching process, the blade array pattern of any of the embodiments of the present invention is etched into the top surface of sheet 6. A second pattern equivalent to the area bounded by each of the openings 8 (e.g., rectangular) is etched into the bottom surface 48 such that each of the blades in the blade array pattern is thinner than the surrounding sheet 6. As a result, the sheet 6 forms a strong base and as the punch deforms the blades 4 downward, each of the blades plastically deforms so as to produce blades that are straighter and more truly perpendicular to the sheet.

In one embodiment of the etching process, a dry resist (e.g., "Dynachem FL" available from Dynachem located in Tustin, Calif.) is applied 12.5 µm thick to one or both sides of the sheet and exposed in a standard manner. Then a suitable spray etcher (e.g., "Dynamil VRP 1 O/NM" available from Western Tech. Assoc. located in Anaheim, Calif.) is used to spray a mixture of ferric chloride and hydrochloric acid onto the resist and sheet at 52° C. (125°F.) for two minutes. A standard caustic stripper is used for the resist removal.

In another embodiment of the etching process, a wet resist (e.g., "Shipley 111S" available from Shipley Corporation, located in Marlborough, Mass.) is applied 7.5 µm thick at about 20° C. (70°F.) to one or both sides of the sheet and exposed in a standard manner. Then a suitable etchant (e.g., ferric chloride) is sprayed onto the resist and sheet at 49° C. (120°F.). A standard caustic stripper is used for the resist removal.

Generally, the blades 4 are at an angle of about 90° to the surface 48 of the sheet 6 after being punched, but they can be disposed at any angle forward or backward from the perpendicular position that will facilitate penetration of and attachment to the stratum corneum. In one embodiment, the blades are all aligned at an angle between about 1° and about 89° degrees, preferably about 10° to about 60°, more preferably about 20° to 45° to facilitate the device being slid along and into the skin. The angled blades have two principal advantages. First, penetration of the blades is not as strongly opposed by the elasticity of the skin because the blades are slid generally horizontally into the skin as opposed to pressing vertically on the skin. Second, the angled blades act to anchor the device in the skin as any motion of the skin is less likely to dislodge the blades. In addition, other anchoring elements such as barbs, openings, etc. can be used with the angled blades to further enhance anchoring of the device.

The sheet and blades can be made from materials that have sufficient strength and manufacturability to produce blades, such as, glasses, ceramics, rigid polymers, metals and metal alloys. Examples of metals and metal alloys include but are not limited to stainless steel, iron, steel, tin, zinc, copper, platinum, aluminum, germanium, nickel, zirconium, titanium and titanium alloys consisting of nickel, molybdenum and chromium, metals plated with nickel, gold, rhodium, iridium, titanium, platinum, and the like. An example of glasses include a devitrified glass such as "PHOTOCERAM" available from Corning in Corning, N.Y. Examples of polymers include but are not limited to polystyrene, polymethylmethacrylate, polypropylene, polyethylene, "BAKELITE", cellulose acetate, ethyl cellulose, styrene/acrylonitrile copolymers, styrene/butadiene copolymers, acrylonitrile/butadiene/styrene (ABS) copolymers, polyvinyl chloride and acrylic acid polymers including polyacrylates and polymethacrylates.

The microblades of the present invention make an elongated, thin microcut (i.e., a slit) in the skin surface because the blades have a small thickness (relative to their width and length) resulting in a minimal blade cross-sectional area for the portions of the blade in the skin. The geometry of the microblades 4 results in minimal blade volume in the skin with maximal blade surface area in the skin. The advantages of the present invention include, but are not limited to: (1) the very sharp first segments on the leading edges make skin penetration easier; (2) the thin blade geometry produces the maximum drug percolation area for a given cross-section of the blade; (3) minimal tissue damage occurs because the amount of blade material in the skin and hence the volume loading is minimized; (4) slanted leading edges (or equivalent pointed shapes) further minimize the amount of volume loading or tissue damage while preserving a large percolation area; (5) for a given volume loading, the larger the surface area, the larger the frictional retaining force in the skin; and (6) for a given desired percolation area, there are fewer blades necessary and therefore the force on each tip is higher making skin penetration easier.

The number of blades and openings of any of the embodiments of the device 2 is variable with respect to the desired flux rate, agent being sampled or delivered, delivery or sampling device used (i.e., electrotransport, passive, osmotic, pressure-driven, etc.), and other factors as will be evident to one of ordinary skill in the art. In general, the larger the number of blades per unit area (i.e., the blade density), the more distributed is the flux of the agent through the skin because there are a greater number of agent-conveying pathways through the skin. Consequently, the smaller the number of blades per unit area, the more concentrated is the flux of the agent through the skin because there are fewer pathways. The present invention has a blade density of at least about 10 blades/cm$^2$ and less than about 1000 blades/cm$^2$, preferably at least about 600 blades/cm$^2$, more preferably at least about 800 blades/cm$^2$. In similar fashion, the number of openings per unit area through which the agent passes is at least about 10 openings/cm$^2$ and less than about 1000 openings/cm$^2$. In one embodiment, the present invention produces a percolation area of about 0.005 to 0.05 cm$^2$/cm$^2$ of body surface, preferably about 0.01 cm$^2$/cm$^2$ of body surface.

One embodiment of the present invention relies on the application of an electric current across the body surface or "electrotransport". Electrotransport refers generally to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent or, for "reverse" electrotransport, samples or enhances sampling of the agent. The electrotransport of the agents into or out of the human body may be attained in various manners. One widely used electrotransport process, iontophoresis, involves the electrically induced transport of charged ions. Electroosmosis, another type of electrotransport process involved in the transdermal transport of uncharged or neutrally charged molecules (e.g., transdermal sampling of glucose), involves the movement of a solvent with the agent through a membrane under the influence of an electric field. Electroporation, still another type of electrotransport, involves the passage of an agent through pores formed by applying an electrical pulse, a high voltage pulse, to a membrane. In many instances, more than one of these processes may be occurring simultaneously to different extents. Accordingly, the term "electrotransport" is given herein its broadest possible interpretation, to include the electrically induced or enhanced transport of at least one charged or uncharged agent, or mixtures thereof, regardless of the specific mechanism(s) by which the agent is actually being transported.

It will be appreciated by those working in the field that the present invention can be used in conjunction with a wide variety of electrotransport systems, as the invention is not limited in any way in this regard. For examples of electrotransport drug delivery systems, reference may be had to U.S. Pat. No. 5,147,296 to Theeuwes et al., U.S. Pat. No. 5,080,646 to Theeuwes et al., U.S. Pat. No. 5,169,382 to Theeuwes et al., and U.S. Pat. No. 5,169,383 to Gyory et al., the disclosures of which are incorporated by reference herein in their entirety. For examples of "reverse" electrotransport devices, references may be had to U.S. Pat. No. 5,279,543 to Glikfeld et al. and U.S. Pat. No. 5,362,307 to Guy et al., the disclosures of which are incorporated by reference herein in their entirety.

Electrotransport devices generally use at least two electrodes which are in electrical contact with some portion of the skin, nails, mucous membranes, or other body surface. In the case of transdermal agent delivery, one of the two electrodes is commonly referred to as the "donor" or "active" electrode, and is the one from which the agent is delivered into the body. In the case of transdermal agent sampling, one of the two electrodes is referred to as the "receptor" electrode, and is the one into which the agent (e.g., body analyte) is collected after being withdrawn from the body. The second electrode is typically termed the "counter" or "return" electrode, and serves to close the electrical circuit through the body. For example, when the agent to be delivered is a cation, i.e., a positively charged ion, the anode becomes the active or donor electrode, while the cathode serves to complete the circuit. Alternatively, if the agent to be delivered is an anion, i.e., a negatively charged ion, the cathode is the donor electrode. When the agent to be sampled is a cation, the cathode becomes the receptor electrode while the anode serves to complete the circuit. When the agent to be sampled is an anion, the anode becomes the receptor electrode while the cathode serves to complete the circuit. When the agent to be sampled has no net charge (e.g., glucose), then either the anode or the cathode, or both electrodes, can serve as the receptor electrode. Both the anode and cathode may be donor electrodes if both anionic and cationic agents are delivered simultaneously. Electrotransport delivery systems generally require at least one reservoir or source of the agent to be delivered to the body. Electrotransport sampling systems likewise require at least one reservoir in which to collect the agent being sampled. Examples of such reservoirs include a pouch or cavity as described in U.S. Pat. No. 4,250,878 to Jacobsen, a porous sponge or pad as described in U.S. Pat. No. 4,141,359 to Jacobsen et al., and a pre-formed gel body as described in U.S. Pat. No. 4,383,529 to Webster, among others. The pertinent portions of which are incorporated herein by reference. Such reservoirs are electrically connected to, and positioned between, the anode or the cathode and the body surface, e.g., to provide a fixed or renewable source of one or more drugs in the case of agent delivery. In addition, electrotransport delivery systems also typically have an electrical power source, e.g., one or more batteries, and an electrical controller designed to regulate the timing, amplitude and/or frequency of the applied electric current, and hence regulate the timing and rate of agemt delivery/sampling. This power source component is electrically connected to the two electrodes. Optional electrotransport device components include a counter reservoir, adhesive coatings, insulating separation layers, and rate-controlling membranes.

Figure 9:
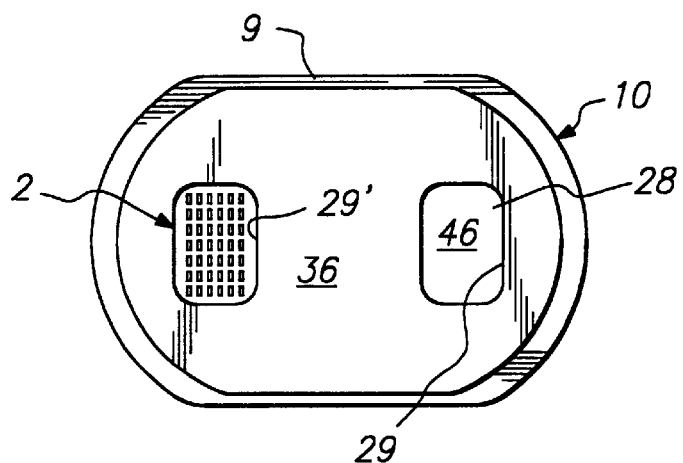
FIG. 9 is a bottom plan view of the electrotransport agent delivery system of FIG. 8.
Figure 8:
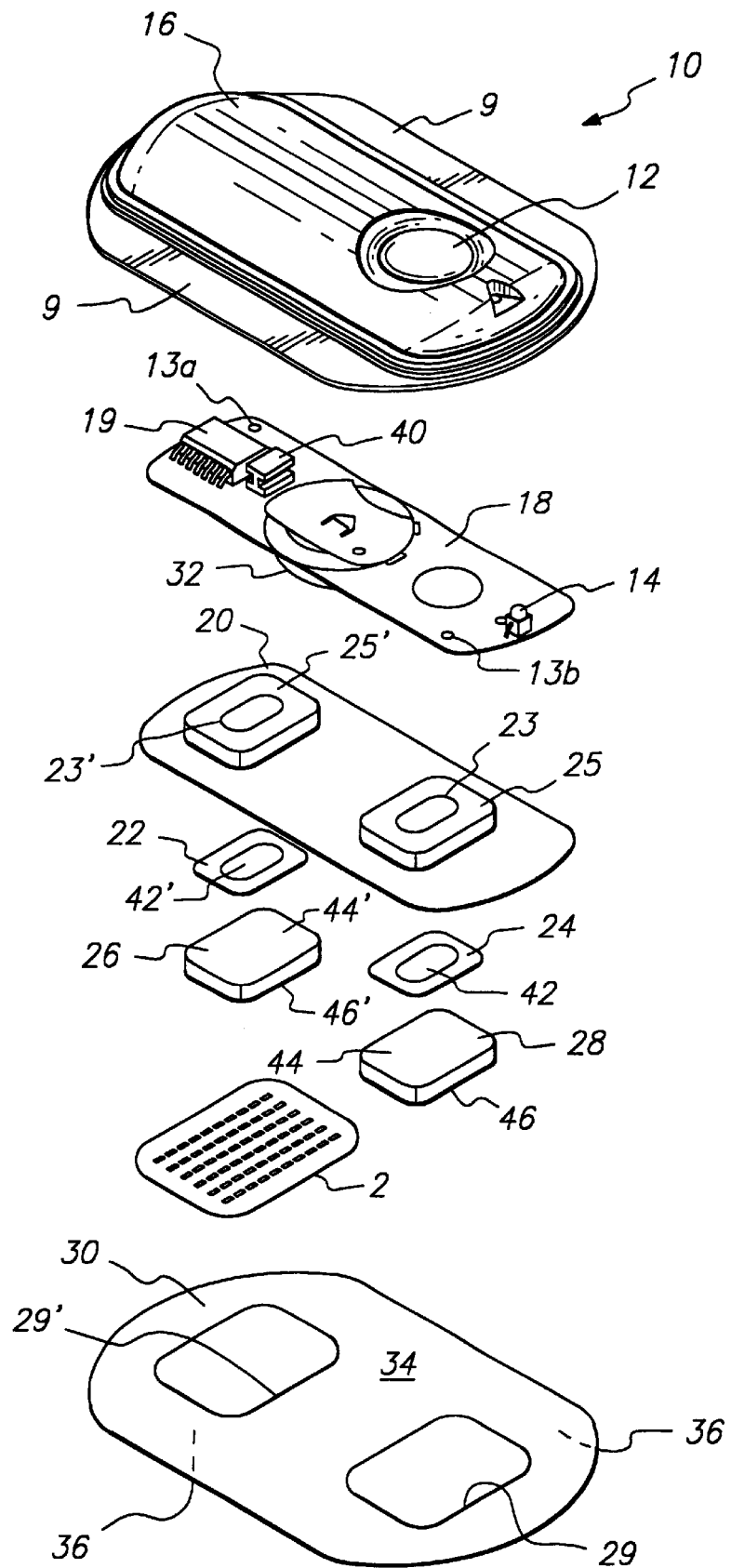
FIG. 8 is a perspective exploded view of one embodiment of an electrotransport agent delivery system with a microblade array device according to the present invention.

FIGS. 8 and 9 illustrate a representative electrotransport delivery/sampling device 10 that may be used in conjunction with the present invention. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 9 which assist in holding device 10 on a patient's skin. Printed circuit board assembly 18 comprises an integrated circuit 19 coupled to discrete components 40 and battery 32. Circuit board assembly 18 is attached to housing 16 by posts (not shown in FIG. 8) passing through openings 13a and 13b, the ends of the posts being heated/melted in order to heat stake the circuit board assembly 18 to the housing 16. Lower housing 20 is attached to the upper housing 16 by means of adhesive layer 30, the upper surface 34 of adhesive layer 30 being adhered to both lower housing 20 and upper housing 16 including the bottom surfaces of wings 9. Shown (partially) on the underside of circuit board assembly 18 is a button cell battery 32. Other types of batteries may also be employed to power device 10 depending on the need.

The device 10 is generally comprised of battery 32, electronic circuitry 19,40, electrodes 22,24, drug/receptor reservoir 26, counter reservoir 28, and member 2, all of which are integrated into a self-contained unit. The outputs (not shown in FIG. 8) of the circuit board assembly 18 make electrical contact with the electrodes 24 and 22 through openings 23,23' in the depressions 25,25' formed in lower housing 20 by means of electrically conductive adhesive strips 42,42'. Electrodes 22 and 24, in turn, are in direct mechanical and electrical contact with the top sides 44',44 of drug reservoirs 26 and 28. The bottom side 46 of drug reservoir 28 contacts the patient's skin through the opening 29 in adhesive layer 30 (FIG. 9). The bottom side 46' of drug reservoir 26 contacts the patient's skin through the plurality of openings 8 in the member 2. The formulation of reservoir 26 is preferably a viscous gel that fills the openings 8 such that the reservoir 26 is in direct contact with the skin when the blades have penetrated the stratum corneum. The contact between the reservoir and skin provides a path for the agent to be transported along. If the reservoir 26 is not in direct contact with the skin initially, typically sweat accumulates in the confined area and provides an agent-transmitting pathway between reservoir 26 and the skin.

Device 10 optionally has a feature which allows the patient to self-administer a dose of drug, or self-sample a body electrolyte, by electrotransport. Upon depression of push button switch 12, the electronic circuitry on circuit board assembly 18 delivers a predetermined DC current to the electrode/reservoirs 22,26 and 24,28 for a delivery interval of predetermined length. The push button switch 12 is conveniently located on the top side of device 10 and is easily actuated through clothing. A double press of the push button switch 12 within a short time period, e.g., three seconds, is preferably used to activate the device, thereby minimizing the likelihood of inadvertent actuation of the device 10. Preferably, the device transmits to the user a visual and/or audible confirmation of the onset of operation by means of LED 14 becoming lit and/or an audible sound signal from, e.g., a "beeper". Agent is delivered/sampled through the patient's skin, e.g., on the arm, by electrotransport over the predetermined delivery interval. Anodic electrode 22 is preferably comprised of silver and cathodic electrode 24 is preferably comprised of silver chloride. Both reservoirs 26 and 28 are preferably comprised of polymeric gel materials. Electrodes 22,24 and reservoirs 26,28 are retained by lower housing 20.

In the case of therpeutic agent (i.e., drug) delivery, a liquid drug solution or suspension is contained in at least one of the reservoirs 26 and 28. Drug concentrations in the range of approximately $1 \times 10^{-4}$ M to 1.0 M or more can be used, with drug concentrations in the lower portion of the range being preferred.

The push button switch 12, the electronic circuitry on circuit board assembly 18 and the battery 32 are adhesively "sealed" between upper housing 16 and lower housing 20. Upper housing 16 is preferably composed of rubber or other elastomeric material, e.g., injection moldable ethylene vinyl acetate. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of an adhesive layer 30 (which has upper adhesive side 34 and body contacting adhesive side 36). The adhesive side 36 covers the entire underneath side of the device 10 except where the member 2 and reservoir 28 are located. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and reservoirs within housing depression 25,25' as well as retains member 2 to lower housing 20 and lower housing 20 to upper housing 16.

In one embodiment of the drug delivery or sampling device there is a release liner (not shown) on the device 10 for maintaining the integrity of the device when it is not in use. In use, the release liner is stripped from the device before the device is applied to the skin.

In other embodiments of the present invention, passive transdermal delivery or sampling devices are used with member 2. In one embodiment the passive transdermal delivery device comprises a reservoir containing agent. The reservoir is preferably in the form of a matrix containing the agent dispersed therein. The reservoir is sandwiched between a backing layer, which is preferably impermeable to the agent, and a rate-controlling membrane. The reservoir is formed of a material, such as a rubbery polymer, that is sufficiently viscous to maintain its shape. If a lower viscosity material is used for the reservoir, such as an aqueous gel, the backing layer and rate-controlling membrane would be sealed together about their periphery to prevent leakage. In a sampling configuration, the reservoir would initially not contain the agent. Located below the membrane is the microblade array member 2. The device adheres to a body surface by means of a contact adhesive layer around the periphery of the member 2. The adhesive layer may optionally contain agent. A strippable release liner (not shown) is normally provided along the exposed surface of the adhesive layer and is removed prior to application of the device to the body surface.

Alternatively, a transdermal therapeutic device in accordance with another embodiment of the present invention can be attached to a body surface by means of a flexible adhesive overlay. In this embodiment, the device is comprised of an agent-containing reservoir (for a delivery configuration) which is preferably in the form of a matrix containing the agent dispersed therein. In a sampling configuration, the reservoir would initially not contain the agent. An impermeable backing layer is provided adjacent one surface of the reservoir. The adhesive overlay maintains the device on the body surface. The adhesive overlay can be fabricated together with, or provided separately from, the remaining elements of the device. With certain formulations, the adhesive overlay may be preferable to the contact adhesive described previously. This is true, for example, where the agent reservoir contains a material (such as, for example, an oily surfactant permeation enhancer) which adversely affects the adhesive properties of the contact adhesive layer. The impermeable backing layer is preferably slightly larger than the reservoir, and in this manner prevents the agents in the reservoir from adversely interacting with the adhesive in the overlay. Optionally, a rate-controlling membrane (not shown) can be provided on the skin/mucosa side of the reservoir. A strippable release liner (not shown) is also normally provided with the device and is removed just prior to application of the device to the body surface.

The formulation for the passive transdermal devices may be aqueous or non-aqueous based. The formulation is designed to deliver the drug at the necessary fluxes. Aqueous formulations typically comprise water and about 1 to 2 weight percent of a hydrophilic polymer as a gelling agent, such as hydroxyethylcellulose or hydroxypropylcellulose. Typical non-aqueous gels are comprised of silicone fluid or mineral oil. Mineral oil-based gels also typically contain 1 to 2 weight percent of a gelling agent such as colloidal silicon dioxide.

The reservoir matrix should be compatible with the delivered agent, any excipients (e.g., flux enhancers, irritation preventing agents) and/or any carrier therefore. When using an aqueous-based system, the reservoir matrix is preferably a hydrophilic polymer, e.g., a hydrogel. When using a non-aqueous-based system, the reservoir matrix is preferably composed of a hydrophobic polymer. Suitable polymeric matrices are well known in the transdermal drug delivery art.

The preferred form in which an agent is delivered or sampled generally determines the type of delivery or sampling system to be used, and vice versa. That is, the selection of a "passive" system which delivers or samples the agent by diffusion or an electrically powered system which delivers or samples the agent by electrotransport will be mostly determined by the form of the agent. For example, with passive delivery systems, it has generally been recognized that the agent is preferably delivered in either its free base or acid form, rather than in the form of a water soluble salt. On the other hand, with electrotransport delivery devices, it has been recognized that the drugs should preferably be ionized and the drug salt should be soluble in water. For the case of pierced skin, there is substantial passive flux through the microslits created by the microblades piercing the stratum corneum. For osmotic and pressure driven systems which deliver or sample drugs by connective flow carried by a solvent, the drug preferably has sufficient solubility in the carrier solvent. It will be appreciated by those working in the field that the present invention can be used in conjunction with a wide variety of osmotic delivery or sampling systems, as the invention is not limited to a particular device in this regard. Osmotic devices are disclosed for example in U.S. Pat. No. 4,340,480 to Eckenhoff, U.S. Pat. No. 4,655,766 to Theeuwes et al., and U.S. Pat. No. 4,753,651 to Eckenhoff, the disclosures of which are incorporated by reference herein in their entirety.

This invention has utility in connection with the delivery of drugs within any of the broad class of drugs normally delivered through body surfaces and membranes, including skin. In general, this includes drugs in all of the major therapeutic areas.

The present invention has particular utility in the delivery of peptides, polypeptides, proteins, nucleotidic drugs, and other such species through body surfaces such as skin. These substances typically have a molecular weight of at least about 300 daltons, and more typically have a molecular weight of at least about 300 to 40,000 daltons. Specific examples of peptides and proteins in this size range include, without limitation, LHRH, LHRH analogs such as goserelin, buserelin, gonadorelin, napharelin and leuprolide, GHRH, GHRF, insulin, insultropin, calcitonin, octreotide, endorphin, TRH, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc), follicle luteoids, aANF, growth factors such as growth factor releasing factor (GFRF), bMSH, GH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

As mentioned above, the member 2 of the present invention can also be used with known sampling devices including, but not limited to, reverse iontophoresis, osmosis, passive diffusion, phonophoresis, and suction (i.e., negative pressure). Osmotic sampling devices can be used to sample any of a variety of agents through a body surface including, but not limited to glucose, body electrolytes, alcohol, blood gases, licit drugs and illicit substances such as drugs of abuse. In another embodiment, an osmotic sampling device is attached to a body surface by means of a flexible adhesive overlay. The osmotic sampling device is comprised of a salt layer located between a semi-permeable or osmotic membrane and an optional agent sensing element. The optional agent sensing element can be any of a variety of chemically reactive sensors and indicators, for example the color indicating test strips associated with glucose testing. The adhesive overlay can have a cut-out or transparent window in the area of the indicators so that the indicators can be readily viewed. In an alternate embodiment, the agent sensing element can be located between the osmotic sampling device and the salt layer.

While the invention has been described in conjunction with the preferred specific embodiments thereof, it is to be understood that the foregoing description is intended to illustrate and not limit the scope of the invention. Other aspects, advantages and modifications within the scope of the invention will be apparent to those skilled in the art to which the invention pertains.

What is claimed is:

1. A device for treating the stratum corneum of a body surface comprising:

a sheet having at least one opening therethrough and a plurality of microblades folded downward from the sheet, at least a portion of the plurality of microblades having a first angled segment located distally on the microblade with a first angle relative to an axis along the length of the microblade, and contiguous with the first angled segment, a second angled segment having an angle relative to the axis greater than the first angle, wherein the width of the microblade at the intersection of the microblade and the sheet is in the range of about 10 microns to about 500 microns and the thickness of the microblade is in the range of about 7 microns to about 100 microns.

2. The device of claim 1, wherein the first angle is in the range of about 1° to 25° and the angle of the second angled segment is in the range of about 26° to 80°.

3. The device of claim 1, wherein the first angle is about 15° and the angle of the second angled segment is about 30°.

4. The device of claim 1, wherein the first angle is about 15° and the angle of the second angled segment is about 35°.

5. The device of claim 1, further comprising a third angled segment contiguous with the second angled segment and having an angle relative to the axis greater than the angle of the second angled segment.

6. The device of claim 1, further comprising a plurality of contiguous angled segments wherein each of the subsequent angled segments progressing proximally along the microblade from the second angled seqment have an angle relative to the axis greater than the angle of the preceding angled segment.

7. The device of claim 1, wherein the first and second angled segments are part of an arc-shaped microblade tip.

8. The device of claim 1, further comprising a therapeutic agent delivery device connected to the treating device and positioned to deliver a therapeutic agent through the opening to the body surface.

9. The device of claim 1, further comprising a sampling device connected to the treating device and positioned to sample a substance from the body surface through the opening.

10. The device of claim 1, wherein the microblades are configured to form pathways in the stratum corneum through which a substance can be introduced or withdrawn.

11. The device of claim 1, wherein at least a portion of the microblade separates the second angled portion from the sheet.

12. The device of claim 1 wherein the length of the microblades is less than about 500 micrometers.

13. A device for treating the stratum corneum of a body surface comprising:

a sheet having at least one opening therethrough and a plurality of microblades located along a periphery thereof and extending downward from the sheet, at least a portion of the plurality of microblades having first angled segments located distally on each side of an axis along the length of the microblade, each of the first segments having a first angle relative to the axis, and contiguous with the first segments, second segments on each side of the axis each having an angle relative to the axis greater than the first angle, wherein the width of the microblade at the intersection of the microblade and the sheet is in the range of about 10 microns to about 500 microns and the thickness of the microblade is in the range of about 7 microns to about 100 microns.

14. The device of claim 13, wherein the first angle of each of the first segments is in the range of about 1° to 25° and the angle of each of the second angled segments is in the range of about 26° to 80°.

15. The device of claim 13, wherein the first angle of each of the first segments is about 15° and the angle of each of the second segments is about 30°.

16. The device of claim 13, wherein the first angle of each of the first segments are not equal angles.

17. The device of claim 13, wherein the angle of each of the second segments are not equal angles.

18. The device of claim 13, further comprising a therapeutic agent delivery device connected to the treating device and positioned to deliver a therapeutic agent through the opening to the body surface.

19. The device of claim 13, further comprising a sampling device connected to the treating device and positioned to sample a substance from the body surface through the openings.

20. The device of claim 13, wherein the microblades are configured to form pathways in the stratum corneum through which a substance can be introduced or withdrawn.

21. The device of claim 13, wherein at least a portion of the microblade separates the second angled portion from the sheet.

22. The device of claim 10, wherein the length of the microblades is less than about 500 micrometers.

23. A device for piercing the stratum corneum of a body surface to form pathways through which an agent can be introduced or withdrawn, comprising:

a sheet having at least one opening therethrough and a plurality of microblades extending downward therefrom, at least a portion of the plurality of microblades having a first angled segment located distally on the microblade with a first angle relative to an axis along the length of the microblade, and contiguous with the first angled segment, a second angled segment having an angle relative to the axis greater than the first angle, and wherein the first angle is about 15° and the angle of the second angled segment is about 30°.

24. A device for piercing the stratum corneum of a body surface to form pathways through which an agent can be introduced or withdrawn, comprising:

a sheet having at least one opening therethrough and a plurality of microblades extending downward therefrom, at least a portion of the plurality of microblades having a first angled segment located distally on the microblade with a first angle relative to an axis along the length of the microblade, and contiguous with the first angled segment, a second angled segment having an angle relative to the axis greater than the first angle, and wherein the first angle is about 15° and the angle of the second angled segment is about 35°.

25. A device for piercing the stratum corneum of a body surface to form pathways through which an agent can be introduced or withdrawn, comprising:

a sheet having at least one opening therethrough and a plurality of microblades extending downward therefrom, at least a portion of the plurality of microblades having a first angled segment located distally on the microblade with a first angle relative to an axis along the length of the microblade, and contiguous with the first angled segment, a second angled segment having an angle relative to the axis greater than the first angle; and a plurality of contiguous angled segments wherein each of the subsequent angled segments progressing proximally along the microblade from the second angled segment have an angle relative to the axis greater than the angle of the preceding angled segment.

26. A device for piercing the stratum corneum of a body surface to form pathways through which an agent can be introduced or withdrawn, comprising:

a sheet having at least one opening therethrough and a plurality of microblades extending downward therefrom, at least a portion of the plurality of microblades having a first angled segment located distally on the microblade with a first angle relative to an axis along the length of the microblade, and contiguous with the first angled segment, a second angled segment having an angle relative to the axis greater than the first angle, and wherein the first and second angled segments are part of an arc-shaped microblade tip.

27. The device of claims 23, 24, 25 or 26, wherein the length of the microblades is less than about 500 micrometers.

* * * * *